US00PP10637P

United States Patent [19]

Kordes

[11] Patent Number: Plant 10,637

[45] Date of Patent: Oct. 13, 1998

[54] SHRUB ROSE PLANT NAMED 'KORCONTA'

[75] Inventor: Wilhelm Kordes, Sparrieshoop, Germany

[73] Assignee: Bear Creek Gardens, Inc., Medford, Oreg.

[21] Appl. No.: 918,423

[22] Filed: Aug. 26, 1997

[51] Int. Cl.[6] ..... A01H 5/00

[52] U.S. Cl. ..... Plt./1

[58] Field of Search ..... Plt./1, 23

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the shrub class, having a vigorous, spreading growth habit; high resistance of fungal diseases; small-leaved, glossy, dark green foliage; large flower clusters; and many glands on peduncles.

1 Drawing Sheet

The present invention relates to a new and distinct variety of rose plant of the shrub class which was originated by me by crossing the variety Yesterday (not patented) with an unnamed seedling of the cross Seafoam×Red Max Graf.

The primary objective of this breeding was to produce a new rose variety having the excellent resistance of its parents to fungal diseases. The objective was substantially achieved, along with other desirable improvements, as evidenced by the following unique combination of characteristics that are outstanding in the new variety and that distinguish it from its parents, as well as from all other varieties of which I am aware:

1. Vigorous, spreading growth habit;
2. Highly resistant to powdery mildew and rust; moderately resistant to blackspot;
3. Small-leaved, glossy, dark green foliage.
4. Flowers in large clusters;
5. Many glands on peduncles.

Asexual reproduction of this new variety by softwood and hardwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Yesterday.

*Pollen parent.*—Unnamed seedling from cross of Seafoam×Red Max Graf.

Classification:

*Botanical.*—Rosa hybrida.

*Commercial.*—Shrub.

Flower

Observations made from specimens grown in a garden environment at Somis, Calif. from January to September 1996.

Blooming habit: Continuous.

Bud:

*Size.*—½-inch long when the petals start to unfurl.

*Form.*—The bud form is long, pointed ovoid.

*Color.*—When sepals first divide, bud color is White Group 155D with Red Group 49D on the bud tip. When half blown, the upper sides of the petals are White Group 155D; and the lower sides of the petals are White Group 155D.

*Sepals.*—Color: Green Group 138B. Surface texture: Covered in fine hairs. There are three normally appendaged sepals. There are two unappendaged sepals with hairy edges.

*Receptacle.*—Color: Green Group 139B. Shape: Apple. Size: Small (3/16×5/16 inch). Surface: Glandular.

*Peduncle.*—Length: Short (½–¾ inch). Surface: Glandular. Color: Medium green or bronzy where exposed to sun. Strength: Stiff, erect.

Bloom:

*Size.*—Small. Average open size is 1¼ inches.

*Borne.*—Several together, in pyramidal clusters of 8 to 20 flowers.

*Stems.*—Short, strong. Average length is about 6 to 10 inches.

*Form.*—When first open: Cupped. Permanence: Flattens.

*Petalage.*—Number of petals under normal conditions: 5.

*Color.*—The upper sides of the petals are White Group 155D. The reverse sides of the petals are White Group 155D. The base of each petal at the point of attachment has a small (1/32×1/32 inch) greenish white dot. The major color on the upper side is White Group 155D.

*Variegations.*—None.

*Discoloration.*—The general tonality at the end of the first day: No change. At the end of the third day: There is an appreciable amount of red pigment expressed, especially around the center of the flower. By day four the petals have dropped.

*Fragrance.*—None.

Petals:

*Texture.*—Thick.

*Shape.*—Deltoid.

*Form.*—Flat.

*Arrangement.*—Imbricated, with no petaloids in the center.

*Persistence.*—Drop off cleanly.

*Lastingness.*—On the plant: Short (3 to 4 days). As a cut flower: Not tested.

Reproductive parts:

*Anthers.*—Size: Medium. Quantity: Many. Color: Yellow. Arrangement: Regular around styles.
*Filaments.*—Color: Yellow.
*Pollen.*—Color: Lemon yellow.
*Styles.*—Color: Greenish.
*Stigmas.*—Color: Greenish white.

Form: Shrub.

Growth: Very vigorous, sprawling. A plant on its own roots in one year will be three feet tall and five feet wide.

Foliage: Number of leaflets on normal mid-stem leaves: 5 or 7.
*Size.*—Small (2½×1¼ to 1½ inches).
*Quantity.*—Abundant.
*Color.*—New foliage: Upper surface is Green Group 137A with some Greyed Red Group 178A on leaf margin; but quickly turning green. Old foliage: Upper surface is Green Group 136A; lower surface is Green Group 136C.

Leaflets:
*Shape.*—Pointed oval.
*Texture.*—Upper side: Leathery, glossy.
*Edge.*—Serrated.
*Serration.*—Single, small.
*Petiole rachis.*—Color: Reddish.
*Petiole underside.*—Rough, with prickles.
*Stipules.*—Medium (¼ inch), serrated, bearded.
*Disease resistance.*—Resistant to mildew and rust and moderately resistant to blackspot under normal growing conditions at Somis, Calif.

Wood:
*New wood.*—Color: Reddish. Bark: Smooth.
*Old wood.*—Color: Green. Bark: Smooth.

Prickles:
*Quantity.*—On main canes from base: Many. On laterals from main canes: Many.
*Form.*—Short (⅛ inch), hooked downward.
*Color when young.*—Red.

Small prickles:
*Quantity.*—On main stalks: Many. On laterals: Many.
*Color.*—Red.

I claim:

1. A new and distinct variety of rose plant of the shrub class, substantially as herein shown and described, characterized particularly as to novelty by the unique combination of its vigorous, spreading growth habit; high resistance to fungal disease; small-leaved, glossy, dark green foliage; large flower clusters; and many glands on peduncles.

* * * * *

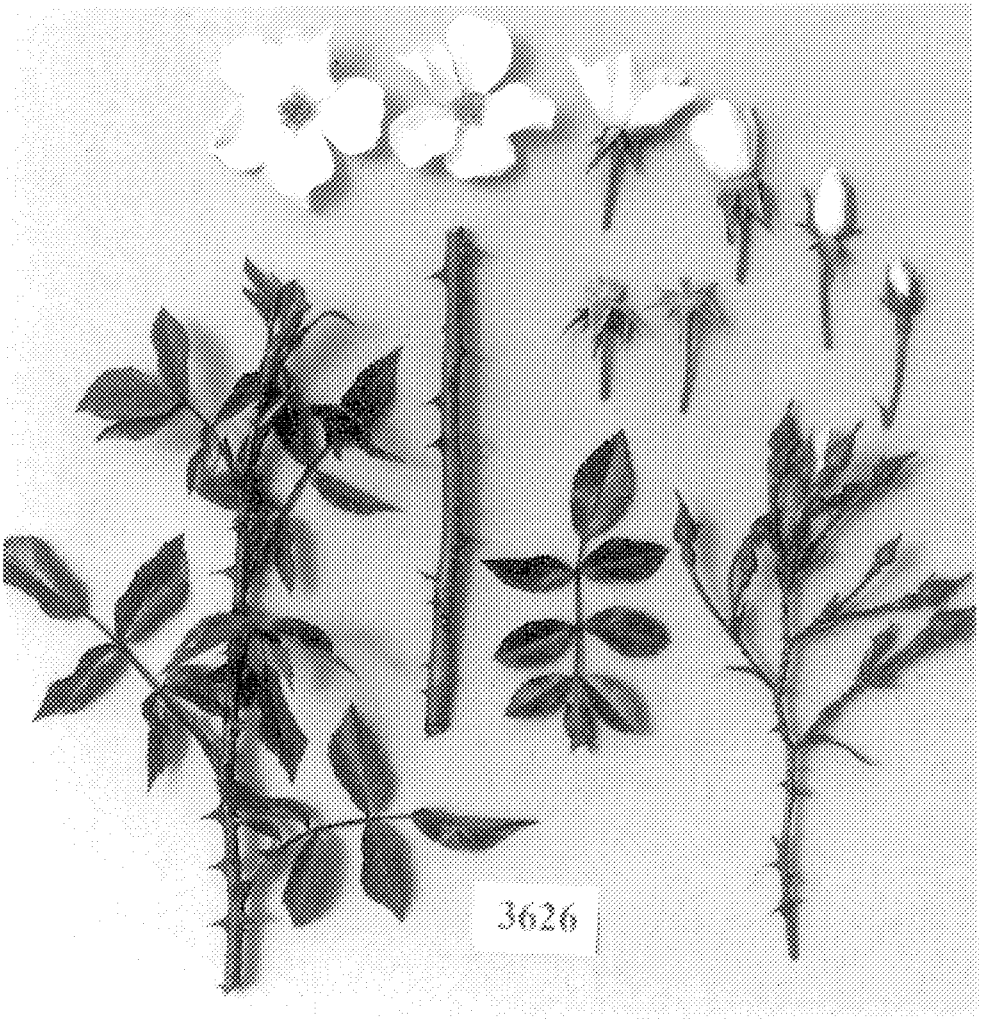
3626